United States Patent [19]

Reiners et al.

[11] Patent Number: 4,752,338

[45] Date of Patent: Jun. 21, 1988

[54] (METH)-ACRYLIC ACID ESTERS

[75] Inventors: Jürgen Reiners, Leverkusen; Jens Winkel, Colonge; Erich Klauke; Carlhans Süling, both of Odenthal; Wolfgang Podszun, Colonge, all of Fed. Rep. of Germany

[73] Assignee: Bayer Aktiengesellschaft, Leverkusen, Fed. Rep. of Germany

[21] Appl. No.: 858,402

[22] Filed: May 1, 1986

[30] Foreign Application Priority Data

May 7, 1985 [DE] Fed. Rep. of Germany ....... 3516257

[51] Int. Cl.$^4$ .......................... C09K 3/00; A61K 5/01
[52] U.S. Cl. ...................... 106/35; 526/246; 560/160; 560/221; 560/027; 560/025
[58] Field of Search .................. 560/027; 106/35; 524/246; 560/160, 027, 221, 025; 433/228

[56] References Cited

U.S. PATENT DOCUMENTS

| 3,718,692 | 2/1973 | Rao | 560/27 |
|---|---|---|---|
| 3,726,886 | 4/1973 | Woo et al. | 560/163 |
| 3,979,426 | 9/1976 | Demajistre | 560/404.5 |
| 4,356,296 | 10/1982 | Griffith et al. | 526/242 |
| 4,388,421 | 6/1983 | Suzuki | 560/221 |
| 4,424,395 | 1/1984 | Strom | 560/133 |
| 4,578,508 | 3/1986 | Griffith | 560/221 |
| 4,628,112 | 12/1986 | Winkel | 560/221 |
| 4,665,217 | 5/1982 | Reiners | 560/221 |

FOREIGN PATENT DOCUMENTS 0041145 12/1981 European Pat. Off. .
3106367 9/1982 Fed. Rep. of Germany .
1321760 6/1973 United Kingdom .

OTHER PUBLICATIONS

Organic Coatings & Plastics Chemistry vol. 42 Mar. 23–28, 1980 American Chemical Society.

Primary Examiner—Paul J. Killos

Attorney, Agent, or Firm—Sprung Horn Kramer & Woods

[57] ABSTRACT (Meth)-acrylic acid esters of the formula

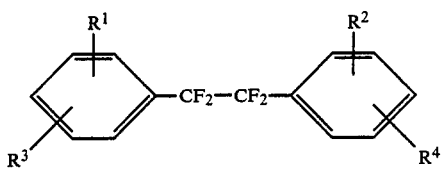

in which
R$^1$ and R$^2$ are each independently hydrogen, chlorine, fluorine or a C$_1$- to C$_4$-alkyl radical and
R$^3$ and R$^4$ are identical or different and represent the group

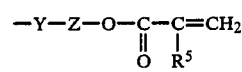

wherein
Y is a divalent bridge member from the group

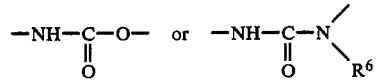

and
Z is a straight-chain or branched hydrocarbon chain which has 2 to 10 carbon atoms, can optionally contain oxygen bridges and is optionally substituted by 1 to 4 acrylate or methacrylate radicals,
wherein
R$^5$ represents hydrogen or methyl and
R$^6$ represents hydrogen, C$_1$-C$_6$- alkyl or phenyl,
which are useful as dental materials.

18 Claims, No Drawings

(METH)-ACRYLIC ACID ESTERS

The invention relates to new fluorine-containing acrylic acid and methacrylic acid esters, called (meth)-acrylic acid esters below, and their preparation. The new compounds can be employed as monomers for use in the dental field.

Fluorine-containing phenylcarbinol-acrylates, such as 1,1,1,3,3,3-hexafluoro-2-phenyl-2-acryloyloxy-propane, are known from Org. Coat. Plast. Chem. 42, 204-207 (1980). (Meth)acrylic acid esters which are built up similarly, such as 1,3-bis-(2-(meth)acryloyl-oxy-1,1,1,3,3,3-hexafluoroprop-2-yl)-5-perfluoroalkylbenzene, and their use in the dental field are described in U.S. Pat. No. 4,356,296. The carbinols are acidified by the trifluoromethyl groups and the carbinol esters prepared therefrom are known to have a reduced stability towards hydrolysis. Their usefulness as dental monomers is thereby limited.

The use of 1,1,5-trihydro-octafluoro-pentyl methacrylate in dental filling compositions is also described in J. Dent. Res. 58, 1181-1186 (1979).

Monomers of this type give dental materials with a low level of mechanical properties.

The compounds of the present invention are (meth)-acrylic acid esters of the formula

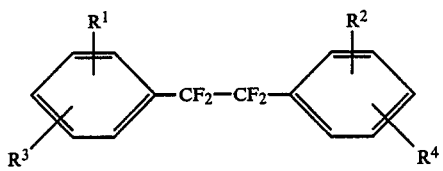

in which
$R^1$ and $R^2$ are identical or different and denote hydrogen, chlorine, fluorine or a $C_1$- to $C_4$-alkyl radical and
$R^3$ and $R^4$ are identical or different and represent the group

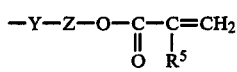

wherein
Y is a divalent bridge member from the group

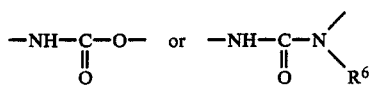

and
Z is a straight-chain or branched hydrocarbon chain which has 2 to 10 carbon atoms, can optionally contain oxygen bridges and is optionally substituted by 1 to 4 acrylate or methayrylate radicals,
wherein
$R^5$ represents hydrogen or methyl and
$R^6$ represents hydrogen, lower alkyl or phenyl.

In the context of the present invention, the substituents can in general have the following meaning.

The alkyl radicals denoted as $R_1$ and $R_2$ in general denote a straight-chain or branched hydrocarbon radical with 1 to 4 carbon atoms. The following alkyl radicals may be mentioned as examples: methyl, ethyl, propyl, isopropyl, butyl and isobutyl.

The lower alkly denoted as $R^6$ denotes a straight-chain or branched hydrocarbon radical with 1 to about 6 carbon atoms. The following lower alkyl radicals may be mentioned as examples: methyl, ethyl, propyl, isopropyl, butyl, isobutyl, pentyl, isopentyl, hexyl and isohexyl.

Z is in general a straight-chain or branched hydrocarbon chain which has 2 to 10 carbon atoms and is substituted by optionally 1 to 4 methacrylate or acrylate radicals. The following hydrocarbon chains may be mentioned as examples: ethylene, propylene, 2-(meth)acryloyloxy-1,3-propylene, 3-(meth)acryloyloxy-1,2-propylene, 2-(meth)acryloyloxymethyl-2-ethyl-1,3-propylene and 2,2-bis-(meth)acryloyloxymethyl-1,3-propylene.

The new (meth)-acrylic acid esters are colorless, have a low volatility and give transparent plastics after polymerization.

They can be used particularly well in sealing agents, adhesives and, preferably, dental materials, such as dental filling compositions and coating agents. The materials thus obtained have a surprisingly high resistance towards physical and chemical stress. Their hardness and breaking strength are particularly improved in comparison with the customary materials employed for this purpose. The advantageous surface properties and the low water absorption of the polymers obtained with the new (meth)-acrylic acid esters are to be particularly emphasized.

Preferred (meth)-acrylic acid esters are compounds of the formula

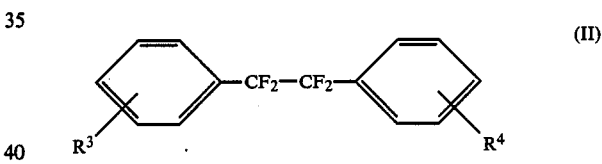

in which
$R^3$ and $R^4$ are identical or different and represent the radical

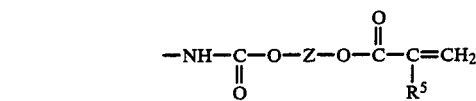

wherein
$R^5$ is hydrogen or methyl and
Z is a straight-chain or branched hydrocarbon chain which has 2 to 10 carbon atoms, can optionally contain oxygen bridges and is optionally substituted by 1 to 4 acrylate or methacrylate radicals.

The substituents $R^3$ and $R^4$ are preferably in the 3,3'- or 3,4'- or 4,4'-position in the 1,2-diphenyl-tetrafluoroethane. Particularly advantageous mechanical values and low monomer viscosities are obtained if mixtures of position isomers are employed. Mixtures with a predominant proportion of 3,3'- or 3,4'-isomers are most suitable.

The substituents $R^3$ and $R^4$ are alkoxycarbonylamino radicals which contain methacrylate groups and can be obtained, for example, by reaction of corresponding isocyanate groups with hydroxy compounds containing methacrylate groups. Preferred compounds are, for example, hydroxyethyl (meth)acrylates, 2-hydroxypropyl (meth)acrylate, trimethylolpropane di(meth)acrylate, propanetriol di(meth)acrylates and pentaerythritol tri(meth)acrylate, and dipentaerythritol penta(meth)acrylate. Hydroxy compounds which contain both acrylate and methacrylate groups are also particularly suitable. Particularly preferred hydroxy compounds are 2-hydroxypropyl methacrylate and propanetriol dimethacrylate (mixture of 1,2- and 1,3-dimethacrylate) and hydroxy-methacryloyloxy-acryloyloxypropane (mixture of 1,2- and 1,3-diester).

The following (meth)-acrylic acid esters may be mentioned as examples:

TABLE 1

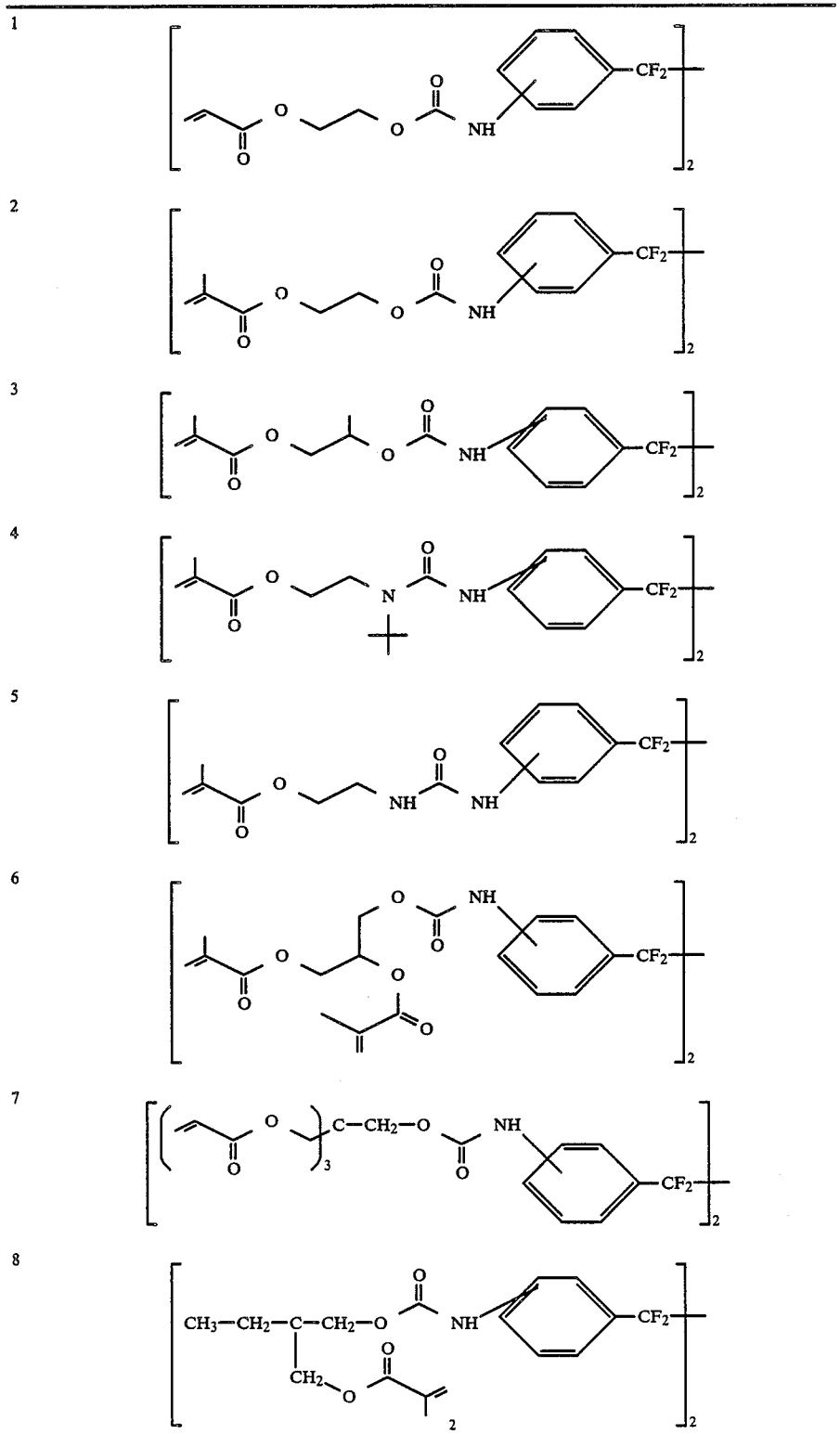

TABLE 1-continued

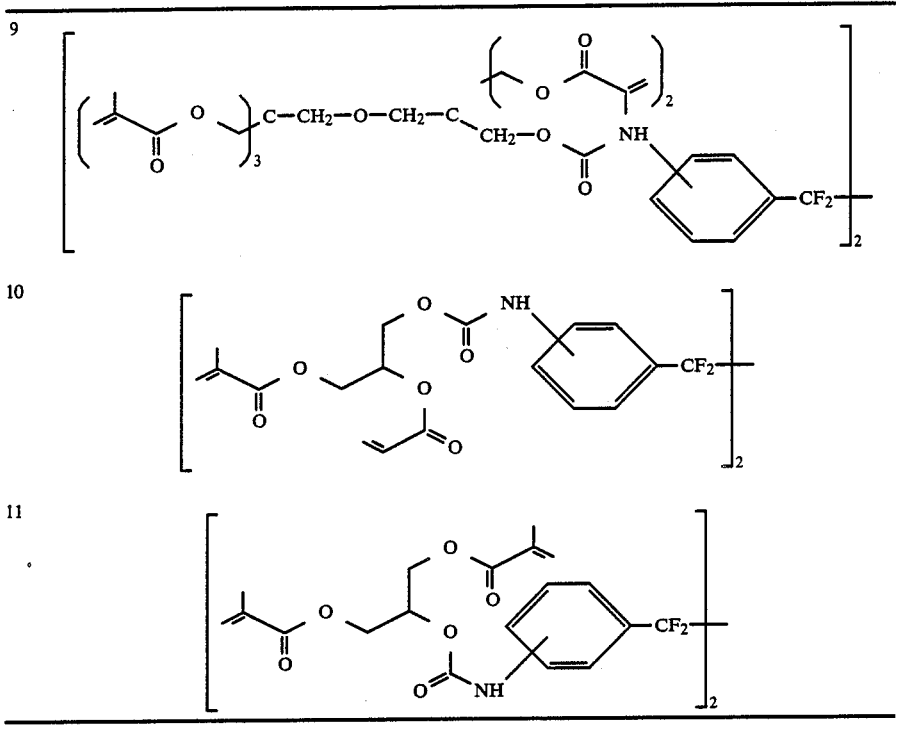

A process has also been found for the preparation of the (meth)-acrylic acid esters according to the invention, which is characterized in that a 1,2-bis-(isocyanatophenyl)-tetrafluoroethane of the formula

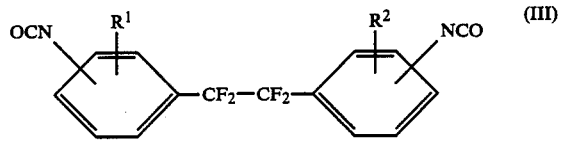

in which $R^1$ and $R^2$ have the abovementioned meaning, is reacted with (meth)-acrylic acid derivatives of the formula

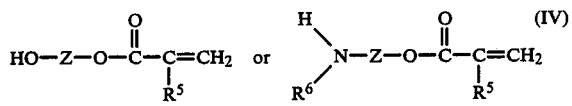

in which

Z is a straight-chain or branched hydrocarbon chain which has 2 to 10 carbon atoms, can optionally contain oxygen bridges and is optionally substituted by 1 to 4 acrylate or methcrylate radicals, $R^5$ is hydrogen or methyl and $R^6$ is hydrogen, lower alkyl or phenyl, in an inert solvent in the presence of a catalyst in the temperature range from 20° to 100° C.

The preparation of the isocyanate compounds of the formula III can be carried out, for example, in accordance with Houben-Weyl, Methoden der Organischen Chemie (Methods of Organic Chemistry) Volume VIII, page 119 et seq. (G. Thieme Verlag, Stuttgart, 1952) by reaction of the corresponding diamino compounds with phosgene (see also: Zh. Obshch. Khim. 32 (9), 3035–3039 (1962) and 35 (9), 1612–1620 (1965) and RA 168274 (1963)).

The reaction of the diisocyanates according to formula III to give the (meth)acrylic acid esters according to the invention is preferably carried out with exclusion of water in an inert solvent. Examples of suitable solvents are: chloroform, tetrahydrofuran, dioxane, methylene chloride, toluene, acetonitrile and freons. Preferred solvents are chloroform, tetrahydrofuran, freon 113 and acetonitrile.

The reaction is in general carried out in the temperature range from 20° to 100° C., preferably 30° to 70° C.

Tin-containing catalysts, such as dibutyl-tin-dilaurate or tin(II) octoate are preferably used to accelerate the reaction. Other suitable catalysts are compounds with tertiary amino groups and titanium compounds. The catalyst is in general employed in an amount of 0.01 to 2.5% by weight, preferably 0.1 to 1.5% by weight, based on the total amount of the reactants.

The process according to the invention is in general advantageously carried out in the presence of 0.01 to 0.2% by weight of a polymerization inhibitor, relative to the total amount of reactants, under normal pressure. However, it is also possible to carry out the process according to the invention under a reduced or increased pressure. A suitable inhibitor is, for example, 2,6-di-tert-.butyl-4-methylphenol. Air, which is passed into the reaction mixture, is also suitable. The process according to the invention can be carried out, for example, as follows:

The reactants are dissolved in the solvent and the catalyst is added, with stirring. The course of the reaction with respect to time can be monitored, for example, by measuring the IR spectra. After complete reaction of the isocyanate groups, the reaction products are isolated by removing the solvent. Prior purification with the aid of adsorbents, for example active charcoal, bleaching earth, silica gel or aluminium oxide, is possible.

For use as monomers for polymeric dental filling compositions or coating agents (dental lacquers) in the dental field, the (meth)-acrylic acid esters of the formula I according to the invention can be mixed with monomers which are known per se, for example in order to adapt the viscosity to suit the intended use. Viscosities in the range from 60 to 10,000 mPas are preferred here. This can be achieved by admixing, if appropriate, a comonomer of low viscosity, as a reactive diluent, with the monomers according to the invention. The compounds according to the invention are employed in the mixture with comonomers in an amount of about 30 to about 90% by weight, an amount of 50 to 90% by weight being particularly preferred.

In the context of the present invention, it is also preferable to employ mixtures of various (meth)-acrylic acid esters according to the invention.

It is also possible to employ monomer mixtures containing several comonomers as reactive diluents.

The following comonomers may be mentioned as examples: triethylene glycol dimethacrylate, tetraethylene glycol dimethacrylate, 1,12-dodecanediol dimethacrylate, 1,6-hexanediol dimethacrylate, diethylene glycol dimethacrylate, 2,2-bis[p-(2'-hydroxy-3'-methacryloyloxypropoxy)phenyl]propane, 2,2-bis[p-(2'-methacryloyloxyethoxy)phenyl]propane, trimethylolpropane tri(meth)-acrylate, bis-(meth)-acryloyloxymethoxymethyl)-tricyclo[5.2.1.0$^{2,6}$]decane (according to DE-OS (German Published Specification) Nos. 2,931,925 and 2,931,926) and the like.

Comonomers which have a boiling point above 100° C. under 13 mbar are particularly preferred.

The (meth)-acrylic acid esters according to the invention, if appropriate mixed with the monomers mentioned, can be hardened to crosslinked polymers by methods which are known per se (G. M. Brauer, H. Argentar, Am. Chem. Soc., Symp. Ser. 212, pages 359-371 (1983)). A system of a peroxidic compound and a reducing agent, for example based on tertiary aromatic amines, is suitable for the so-called redox polymerization. Examples of peroxides are: dibenzoyl peroxide, dilauroyl peroxide and di-4-chlorobenzoyl peroxide.

Examples which may be mentioned of tertiary aromatic amines are N,N-dimethyl-p-toluidine, bis-(2-hydroxyethyl)-p-toluidine, Bis(2-hydroxyethyl)-3,5-dimethylaniline and the N-methyl-N-(2-methylcarbamoyloxypropyl)-3,5-dimethylaniline described in German Patent Specification No. 2,759,239.

The concentrations of the peroxide and of the amine are advantageously chosen such that they are 0.1 to 5% by weight, preferably 0.5 to 3% by weight, relative to the monomer mixture. The peroxide-containing and amine-containing monomer mixtures are stored separately until used.

The monomers according to the invention can also be brought to polymerization by irradiation with UV light or visible light (for example in the wavelength range from 230 to 650 nm). Examples of suitable initiators for photoinitiated polymerization are benzil, benzil dimethyl ketal, benzoin monoalkyl ethers, benzophenone, p-methoxybenzophenone, fluorenone, thioxanthone, phenanthrenequinone and 2,3-bornanedione (camphorquinone), if appropriate in the presence of photoactivators which act as synergists, such as N,N-dimethylaminoethyl methacrylate, triethanolamine or 4-N,N-dimethylaminobenzenesulphonic acid bisallylamide. The procedure for the photopolymerisation process is described, for example, in German Patent Specification No. 3,135,115.

In addition to the initiators described above, light stabilizers and polymerization inhibitors known per se for this intended use can be added to the (meth)-acrylic acid esters according to the invention.

The light stabilizer and the polymerization inhibitor are in each case in general employed in an amount of 0.01 to 0.50 parts by weight per 100 parts by weight of the monomer mixture. The monomer mixtures can be employed as coating agents (dental lacquers) without the addition of fillers.

When used as dental filling compositions, fillers are in general added to the resulting monomer mixtures. In order to be able to achieve a high degree of filling, monomer mixtures which have a viscosity in the range from 60 to 10,000 mPas are particularly advantageous. Inorganic fillers can preferably be admixed with the monomer mixtures containing the compounds of the formula I according to the invention. Examples which may be mentioned are rock crystal, quartzite, cristobalite, quartz glass, highly disperse silicic acid, aluminium oxide and glass ceramics, for example glass ceramics containing lanthanum and zirconium (DE-OS (German Published Specification) No. 2,347,591).

The inorganic fillers are preferably pretreated with an adhesion promoter to improve bonding to the polymer matrix of the polymethacrylate. Adhesion promotion can be achieved, for example, by treatment with organosilicon compounds (E. P. Plueddemann, Progress in Organic coatings, 11, 297 to 308 (1983)). 3-Methacryloyloxypropyl-trimethoxysilane is preferably employed.

The fillers for the dental filling compositions according to the invention in general have an average particle diameter of 0.01 to 100 μm, preferably 0.05 to 50 μm and particularly preferably 0.05 to 5 μm. It may also be advantageous to employ several fillers with different particle diameters side by side.

The filler content in the dental filling compositions is in general 5 to 85% by weight, preferably 50 to 80% by weight.

To prepare the dental filling compositions, the components are processed using commercially available kneading machines.

The amount of (meth)-acrylic acid esters according to the invention in the filling compositions is in general 5 to 85% by weight, relative to the filling composition.

EXAMPLE 1

Preparation of 1,2-bis-(3-isocyanatophenyl)-1,1,2,2-tetrafluoroethane

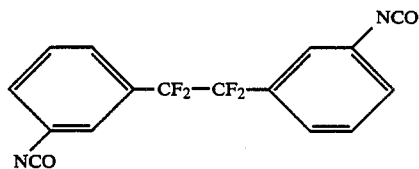

621 g of phosgene are condensed in 2.3 l of chlorobenzene at about 0° C. 353 g of 1,2-bis(3-aminophenyl)-1,1,2,2-tetrafluoroethane, dissolved in 1.2 l of chlorobenzene, are slowly added at a temperature of −10° C. to +10° C. The batch is heated up to 120° C. in the course of four hours. Further gaseous phosgene is passed in from about 80° C. The solution becomes clear at 100° to 110° C. Phosgene is passed through the solution at 120° C. for a further 90 minutes. The phosgene still dissolved is then blown out with $CO_2$ and the mixture is subsequently worked up by distillation. 355 g of 1,2-bis-(3-isocyanatophenyl)-1,1,2,2-tetrafluoroethane, boiling point: 145° to 150° C./0.1 mbar, melting point: 139° to 140° C. (purity, according to gas chromatography, 97%) are obtained.

If a non-purified diamine, such as is obtained by hydrogenation of the corresponding non-recrystallized dinitro compound, is employed for the phosgenation, the same process for phosgenation of the base as above gives the diisocyanate with a content of about 80%. Melting point: 128° to 135° C.

A diisocyanate mixture of the 1,2-diphenyl-1,1,2,2-tetrafluoroethane containing only about 45% of pure 3,3'-diisocyanate is obtained if the pure 3,4-compound is separated off from the mixture of the corresponding dinitro compounds by recrystallization from toluene and the mother liquors thus obtained are worked up, hydrogenated, and phosgenated as described above.

The melting range of the distilled diisocyanate mixture is 117° to 127° C.

EXAMPLE 2

(3,3'-isomer of the compound 2 from Table 1)

Preparation of

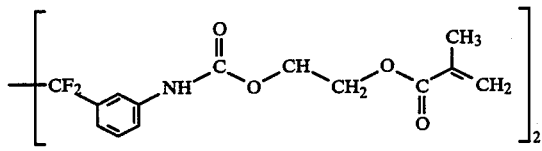

16.8 g (50 mmol) of 1,2-bis-(3-isocyanatophenyl)-1,1,2,2-tetrafluoroethane from Example 1 are suspended in 100 ml of acetonitrile. 50 mg of dibutyl-tin dilaurate are added. After warming to 50° C., 13 g (100 mmol) of 2-hydroxyethyl methacrylate are added dropwise. For stabilization, air is passed through the reaction mixture. The course of the reaction is monitored by IR spectroscopy until the absorption band of the isocyanate group has disappeared. The reaction time is about 36 hours, but can be shortened further by increasing the temperature or using tin(II) octoate.

For working up, some of the solvent is removed in vacuo and the suspension is filtered.

The solid which remains (17.5 g; 58.7%) has the expected structure, on the basis of the $^1$H-NMR data. Melting point: 160° C.

EXAMPLE 3

3,3'-isomer of compound 3 from Table 1

Preparation of

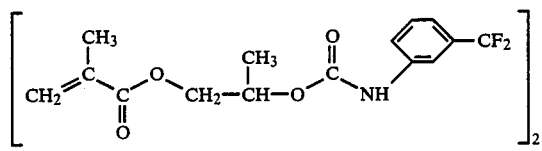

100.8 g (0.3 mole) of 1,2-bis-(3-isocyanatophenyl)-1,1,2,2-tetrafluoroethane are suspended in 500 ml of chloroform. 1 g of dibutyl-tin dilaurate and 80 mg of 2,5-di-tert.butyl-4-methylphenol are added. 86.4 g (0.6 mole) of 2-hydroxypropyl methacrylate are added dropwise to the solution which has been warmed to 50° to 60° C. When the reaction has ended, a clear solution which is slightly yellow-coloured is present. The solution is stirred with active charcoal, and this is filtered off over Celite. The filtrate is freed from the solvent. The yield is virtually quantitative. The product is present as a colourless viscous liquid.

The structure given above is confirmed on the basis of the IR and $^1$H-NMR spectra.

The molecular weight was determined as 625 by osmometry (calculated: 624).

EXAMPLE 4

(compound 3 from Table 1)

If a mixture of 1,2-bis-(3-isocyanatophenyl)-1,1,2,2-tetrafluoroethane and 1,2-bis-(4-isocyanatophenyl)-1,1,2,2-tetrafluoroethane is used as the starting substance, the meta/para isomer mixture is formed in an analogous manner to Example 3.

EXAMPLE 5

(Mixture of the isomeric compounds 6 and 11 from Table 1)

Reaction of 1,2-bis-(isocyanatophenyl)-1,1,2,2-tetrafluoroethane with bis-(methacryloxy)-hydroxypropane (isomer mixture).

67.2 g (200 mmol) of an isomer mixture of bis-(3-isocyanatophenyl)-1,1,2,2-tetrafluoroethane and bis-(4-isocyanatophenyl)-1,1,2,2-tetrafluoroethane are suspended in 200 ml of chloroform, and 0.4 g of dibutyl-tin dilaurate and 0.063 g of 2,5-di-tert.butyl-4-methylphenol are added. The mixture is warmed to 50° C. 91.2 g (400 mmol) of bis(methacryloxy)-hydroxy-propane are added dropwise at this temperature.

Complete conversion has been achieved after a reaction time of 3 hours. The reaction mixture is worked up as in Example 3. The product is a colourless viscous liquid. Molecular weight (osmometry): 787.

USE EXAMPLES

EXAMPLE 6

Preparation of coating solutions (a) Redox-hardening system 1.94% by weight of di-benzoyl peroxide are dissolved in a solution of the monomer mentioned in Example 3 (70 parts) and triethylene glycol dimethacrylate (30 parts) (corresponding to 0.008 mole of peroxide per 100 g of monomer mixture).

2% by weight of N-methyl-N-(2methylcarbamoyloxypropyl)-3,5-dimethylaniline (German Patent Specification No. 2,759,239) is dissolved in a second mixture which contains no peroxide but otherwise has the same composition.

A mixture of equal parts of the two solutions described above hardens in 2 to 3 minutes.

The mechanical properties of various monomers are shown in Table 2.

(b) Photohardening system 0.5% by weight of 4-N,N-dimethylaminobenzenesulphonic acid bis-allylamide, 0.125% by weight of benzil dimethyl ketal and 0.2% by weight of bicyclo[2,2,1]-1,7,7-trimethyl-heptane-2,3-dione (2,3-bornanedione)

are dissolved in a monomer mixture of the composition described under (a) (without peroxide).

On exposure with a dental lamp, the liquid hardens (exposure time 40 seconds).

EXAMPLE 7

Example 6 is repeated using the monomer from Example 5, but 32.8 parts by weight of triethylene glycol dimethacrylate are used.

The coating agent from Example 6 was subjected to testing of the flexural strength and flexural modulus in accordance with DIN 13922.

EXAMPLE 9

Example 8 was repeated using the coating agent from Example 7.

The measurement results from Example 8 and Example 9 are summarized in Table 2.

TABLE 2

Testing of the coating solutions from Examples 6 and 7 (unless indicated otherwise, the polymerization activation corresponds to that of Example 6 and 7)

| Composition of the coating agent (parts by weight) | | | | Flexural strength [N/mm$^2$] | Flexural modulus [N/mm$^2$] | Wallace penetration depth [mm] |
|---|---|---|---|---|---|---|
| (A) | 70 parts | Monomer from Example 3 | | | | |
|  | 30 parts | TEGDMA* | | | | |
|  |  | redox-hardening | 1.6% of peroxide 1.7% of amine | 95.3 | 5982 | — |
|  |  | redox-hardening | | 100.0 | | 0.0161 + 0.0003 |
|  |  | photo-hardening | | | | 0.0140 + 0.0007 |
| (B) | 67.2 parts | Monomer from Example 5 | | | | |
|  | 32.8 parts | TEGDMA* | | | | |
|  |  | redox-hardening | | | | 0.0156 + 0.0017 |
|  |  | photo-hardening | | 90.4 | 2115 | 0.0149 + 0.0011 |
| (C) | 67.2 parts | Bis-GMA (comparison) | | | | |
|  | 32.8 parts | TEGDMA* | | | | |
|  |  | redox-hardening | | | | 0.0169 + 0.0011 |
|  |  | photo-hardening | | 71.2 | 1995 | 0.0152 + 0.0018 |

*TEGDMA = triethylene glycol dimethacrylate
Bis-GMA = bisphenol A diglycidyl dimethacrylate (= 2,2-bis[p-(2'-hydroxy-3'-methacryloyloxy-)propoxyphenyl]propane

EXAMPLE 8

Testing of the coating solutions from Examples 6 and 7

(a) Wallace hardness test

Sample preparation for the redox-hardening coating solution:

The two solutions described in Example 6(a) and in each case containing amine or peroxide are mixed in a weight ratio of 1:1 for 30 seconds and poured into an annular mold covered with a metal plate (coated with polyamide film). After the sample has hardened, a second metal plate covered with polyamide film is placed on top. The metal plates are pressed together with the aid of a clamp. The mold is placed in a waterbath at 37° C. for 135 minutes. Thereafter, the test pieces are removed and abraded on both sides with silicon carbide paper (1,000). Sample preparation for the photo-hardening coating solution:

The solution described in Example 6(b) is poured into an annular mold covered with a polyamide film and, after a second film has been placed on top, is hardened by irradiation (on both sides for 60 seconds) with a dental lamp. The subsequent procedure is as for the redox-hardened test piece.

The Wallace penetration depth is measured in the period from 15 to 45 minutes after hardening of the samples. A Vickers pyramid is thereby pressed on under an initial load of 1 g for 15 seconds and then under a main load of 100 g for 60 seconds.

A penetration depth of the diamond under the action of the main load is recorded as the Wallace penetration depth ($H_w$ 100/60) in $\mu$m. In each case 5 measurements are used for evaluating a sample.

(b) Testing of the mechanical properties

EXAMPLE 9

Preparation of a redox-hardening dental filling composition

Amine paste: 2.0% by weight of N-methyl-N-(2-methylcarbamoyloxypropyl)-3,5-dimethylaniline is dissolved in a mixture of 70 parts by weight of the compound from Example 3 according to the invention and 30 parts by weight of triethylene glycol dimethacrylate. 5 g of this solution are processed to a paste with 15 g of a commercially available glass ceramic which has an average particle diameter of 4 $\mu$m and has been silanized with 3-methacryloyloxypropyltrimethoxysilane.

Peroxide paste: 1.94% by weight of dibenzoyl peroxide is dissolved in a mixture of 70 parts by weight of the compound from Example 3 according to the invention and 30 parts by weight of triethylene glycol dimethacrylate. 5 g of this solution are processed to a paste with 15 g of a commercially available glass ceramic which has an average particle diameter of 4 $\mu$m and has been silanized with 3-methacryloyloxypropyl-trimethoxysilane.

A mixture of equal parts of amine paste and peroxide paste hardens within 2 to 3 minutes.

EXAMPLE 10

Preparation of a photo-hardening dental filling material 0.2% by weight of 2,3-bornanedione, 0.125% by weight of benzil dimethyl ketal and 0.5% by weight of 4-N,N-dimethylaminobenzenesulphonic acid bis-allylamide are dissolved in a mixture of 70 parts by weight of the monomer from Example 3 and 30 parts by weight of triethylene glycol dimethacrylate.

5 g of this solution are processed to a paste with 15 g of the filler described in Example 9 (filler content of 75%).

Hardening is carried out by exposure with a dental lamp from Kulzer. With an exposure time of 40 seconds, the hardening depth is 6 mm.

EXAMPLE 11

Example 10 is repeated using the monomer from Example 5, but 32.8 parts by weight of triethylene glycol dimethacrylate are used.

EXAMPLE 12

Testing of the dental compositions from Example 10 and 11

Testing of the flexural strength and flexural modulus is carried out in accordance with DIN 13922. The results are summarized in Table 3.

TABLE 3

Mechanical properties of dental compositions (photo-activation according to Example 10 and 11)

| Monomer mixture | | Filler content | Flexural strength [N/mm$^2$] | Flexural modulus [N/mm$^2$] |
|---|---|---|---|---|
| 70 parts | Monomer from Example 3 | 75% of glass ceramic | 143.5 | 12890 |
| 30 parts | TEGDMA* | | | |
| 67.2 parts | Monomer from Example 5 | 75% of glass ceramic | 128.7 | 13250 |
| 32.8 parts | TEGDMA* | | | |

*TEGDMA = triethylene glycol dimethacrylate

EXAMPLE 13

Measurement of surface tensions of solids

Surface tension measurements were carried out on the coating agents, hardened by photo-induced polymerization, of Examples 6 and 7. The dynamic wetting properties of liquids on the surfaces of the solids was determined by means of a video system. The surface tensions were calculated from the initial wetting angles of 5 test liquids. The results are summarized in Table 4.

TABLE 4

Measurement of the surface tensions of the solids

| Monomer from Example | Ratio of monomer to TEGDMA* | Total [mN/m] | Non-polar content [mN/m] | Polar content [mN/m] | Polar content [%] |
|---|---|---|---|---|---|
| 3 | 60/40 | 39.7 | 30.2 | 9.5 | 23.9 |
| 3 | 77/23 | 39.6 | 33.8 | 5.8 | 14.6 |
| 5 | 67.2/32.8 | 40.7 | 35.2 | 5.5 | 13.5 |
| Comparison (Bis-GMA) | 67.2/32.8 | 42.2 | 28.7 | 13.5 | 32.0 |

*TEGDMA = triethylene glycol dimethacrylate

It will be understood that the specification and examples are illustrative but not limitative of the present invention and that other embodiments within the spirit and scope of the invention will suggest themselves to those skilled in the art.

What is claimed is:

1. A dental filling composition, comprising (meth)-acrylic acid esters of the formula

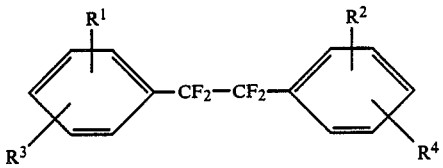

in which $R^1$ and $R^2$ are identical or different and denote hydrogen, chlorine, fluorine or a $C_1$- to $C_4$-alkyl radical and $R^3$ and $R^4$ are identical or different and represent the group

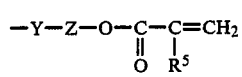

wherein

Y is a divalent bridge member from the group

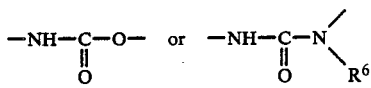

and

Z is a straight-chain or branched hydrocarbon chain which has 2 to 10 carbon atoms, can optionally contain oxygen bridges and is optionally substituted by 1 to 4 acrylate or methacrylate radicals, wherein $R^5$ represents hydrogen or methyl and $R^6$ represents hydrogen, $C_1$-$C_6$-alkyl or phenyl and a dental filler.

2. In a method of coating a dental surface with a coating solution the improvement wherein the coating solution contains a (meth)-acrylic acid ester of the formula

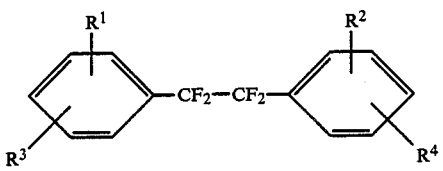

in which $R^1$ and $R^2$ each independently are hydrogen, chlorine, fluorine or a $C_1$- to $C_4$-alkyl radical and $R^3$ and $R^4$ each independently represent the group

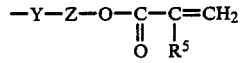

wherein

Y is a divalent bridge member from the group

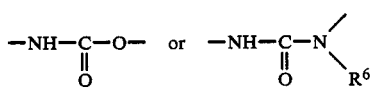

and

Z is an aliphatic hydrocarbon chain which has 2 to 10 carbon atoms, and which can optionally contain oxygen bridges and is optionally substituted by 1 to 4 acrylate or methacrylate radicals,
wherein
$R^5$ is hydrogen, or methyl and
$R^6$ is hydrogen, $C_1$- to $C_6$-alkyl or phenyl.

3. In a method of providing a dental filling with a dental filling material the improvement wherein the dental filling material contains a (meth)-acrylic acid ester of the formula

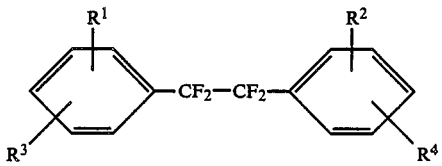

in which
$R^1$ and $R^2$ each independently are hydrogen, chlorine, fluorine or a $C_1$- to $C_4$-alkyl radical and
$R^3$ and $R^4$ each independently represent the group

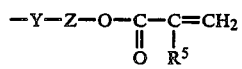

wherein
Y is a divalent bridge member from the group

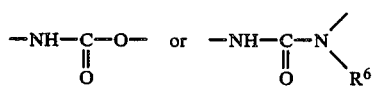

and
Z is an aliphatic hydrocarbon chain which has 2 to 10 carbon atoms, and which can optionally contain oxygen bridges and is optionally substituted by 1 to 4 acrylate or methacrylate radicals,
wherein
$R^5$ is hydrogen or methyl and
$R^6$ is hydrogen, $C_1$- to $C_6$-alkyl or phenyl.

4. A dental filling composition according to claim 1, comprising a (meth)-acrylic acid ester of the formula

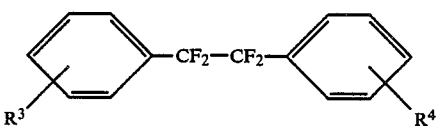

in which
$R^3$ and $R^4$ each independently represent one of the radicals

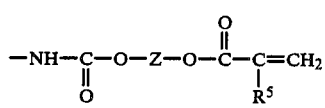

wherein
$R^5$ is hydrogen or methyl and
Z is an aliphatic hydrocarbon chain which has 2 to 10 carbon atoms, and which can optionally contain oxygen bridges and is optionally substituted by 1 to 4 acrylate or methacrylate radicals.

5. A dental filling composition according to claim 1, wherein said (meth)-acrylic acid ester has the formula

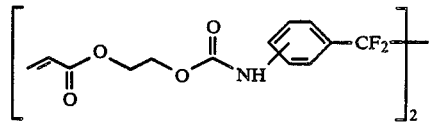

6. A dental filling composition according to claim 1, wherein said (meth)-acrylic acid ester has the formula

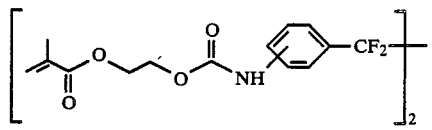

7. A dental filling composition according to claim 1, wherein said (meth)-acrylic acid ester has the formula

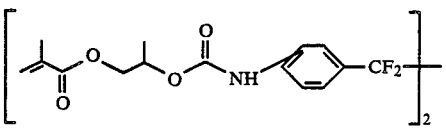

8. A dental filling composition according to claim 1, wherein said (meth)-acrylic acid ester has the formula

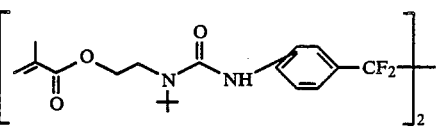

9. A method of coating according to claim 2, wherein said (meth)-acrylic acid ester has the formula

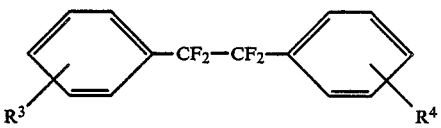

in which
$R^3$ and $R^4$ each independently represent one of the radicals

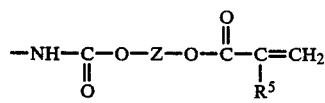

wherein
$R^5$ is hydrogen or methyl and
Z is an aliphatic hydrocarbon chain which has 2 to 10 carbon atoms, and which can optionally contain oxygen bridges and is optionally substituted by 1 to 4 acrylate or methacrylate radicals.

10. A method of coating according to claim 2, wherein said (meth)-acrylic acid ester has the formula

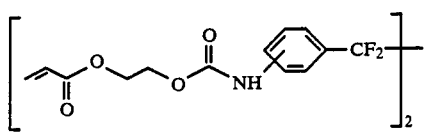

11. A method of coating according to claim 2, wherein said (meth)-acrylic acid ester has the formula

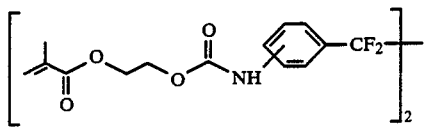

12. A method of coating according to claim 2, wherein said (meth)-acrylic acid ester has the formula

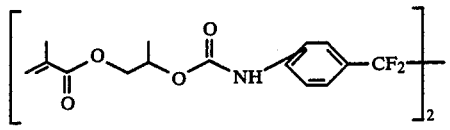

13. A method of coating according to claim 2, wherein said (meth)-acrylic acid ester has the formula

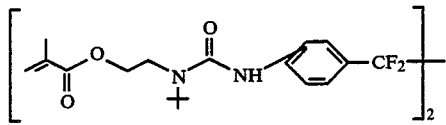

14. A method of providing a dental filling according to claim 3, wherein said (meth)-acrylic acid ester has the formula

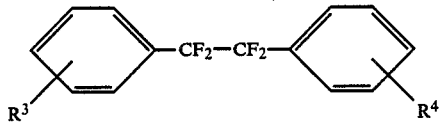

in which
$R^3$ and $R^4$ each independently represent one of the radicals

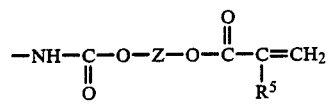

wherein
$R^5$ is hydrogen or methyl and
Z is an aliphatic hydrocarbon chain which has 2 to 10 carbon atoms, and which can optionally contain oxygen bridges and is optionally substituted by 1 to 4 acrylate or methacrylate radicals.

15. A method of providing a dental filling according to claim 3, wherein said (meth)-acrylic acid ester has the formula

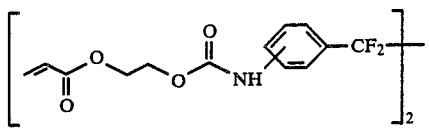

16. A method of providing a dental filling according to claim 3, wherein said (meth)-acrylic acid ester has the formula

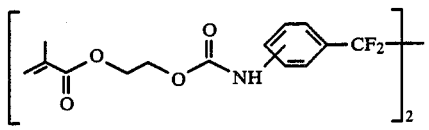

17. A method of providing a dental filling according to claim 3, wherein said (meth)-acrylic acid ester has the formula

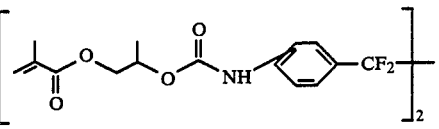

18. A method of providing a dental filling according to claim 3, wherein said (meth)-acrylic acid ester has the formula

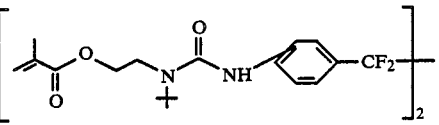

* * * * *